(12) United States Patent
Segueilha

(10) Patent No.: US 6,365,383 B1
(45) Date of Patent: Apr. 2, 2002

(54) METHOD OF PRODUCING ERYTHRITOL BY REPEATED FED-BATCH FERMENTATION

(75) Inventor: Laurent Segueilha, Armentieres (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/337,909

(22) Filed: Jun. 22, 1999

(30) Foreign Application Priority Data

Jun. 24, 1998 (FR) .............................. 98 07998

(51) Int. Cl.$^7$ .................................. C12P 7/18
(52) U.S. Cl. ................. 435/158; 435/155; 435/157; 435/169; 435/170; 435/171
(58) Field of Search ................. 435/158, 177, 435/170, 169, 155, 157

(56) References Cited

U.S. PATENT DOCUMENTS

| 4,923,812 A | 5/1990 | Horikita et al. |
| 4,939,091 A | * 7/1990 | Sasaki et al. ............... 435/158 |

FOREIGN PATENT DOCUMENTS

| EP | 0 136 802 | 4/1985 |
| EP | 0 136 803 | 4/1985 |
| EP | 0 327 342 | 8/1989 |
| EP | 0 136 804 | 10/1991 |

OTHER PUBLICATIONS

Crueger et al, *Biotechnology: A Textbook of Industrial Microbiology*, 2d Ed., Sinaver Associates, Inc., Sunderland, Mass pp. 67–70, 1989.*
Abstract + claims Derwent J 61031091.
Roxburgh et al., 1956, Canadian Journal Technology, vol. 34, pp. 248–253.

* cited by examiner

*Primary Examiner*—Francisco Prats
(74) *Attorney, Agent, or Firm*—Henderson & Sturm LLP

(57) ABSTRACT

The invention relates to a method of producing erythritol by fed-batch and repeated fermentation of sugars by microorganisms which produce erythritol, characterised by the fact that the fermentation is started by introducing said microorganisms into a fermentation medium containing a concentration of sugars lower than 200 g/l, and the fermentation is continued by carrying out at least one fermentation cycle which comprises:

- at least one phase of adding substrates so as to maintain the concentration of total sugars at a value of between 0 and 200 g/l,
- at least one phase of separation of the fermentation medium into a concentrated fraction of microorganisms and another fraction enriched with erythritol, when there is total consumption of sugars,
- at least one phase of recycling recovered and concentrated microorganisms in the fermentation medium.

2 Claims, No Drawings

METHOD OF PRODUCING ERYTHRITOL BY REPEATED FED-BATCH FERMENTATION

FIELD OF THE INVENTION

The present invention relates to a method of producing erythritol by fed-batch and repeated fermentation of sugars by microorganisms which produce erythritol.

BACKGROUND OF THE INVENTION

By fed-batch fermentation is meant a fermentation in which microorganisms are fed by the successive addition of substrates, and in which the product and the co-products of the fermentation remain in the medium until the end of fermentation.

By repeated fed-batch fermentation is meant a fed-batch fermentation in which the fraction of the fermentation medium containing the microorganisms is removed in order to use it as an inoculum for a following fed-batch fermentation.

The term substrates is defined as being all the nutritive elements which are introduced into the fermentation media. In the sense of the invention, the substrates are principally carbonaceous and nitrogenous sources which may be directly assimilated by the microorganisms producing erythritol.

The industrial preparation of erythritol is based principally on fermentation methods which use yeasts or unicellular fungi, and this from hydrocarbons or from sugars as directly assimilable sources of carbon.

By sugars is meant in the present invention all the carbonaceous sources which may be directly assimilated by the microorganisms which produce erythritol. Such sugars are chosen for example from the group consisting of glucose, saccharose, fructose, maltose, xylulose and maltulose, on their own or in a mixture. By extension, sugars also means certain sugar alcohols (or polyols) such as mannitol or sorbitol which, being assimilated by said microorganisms, will also lead to the production of erythritol.

The microorganisms producing erythritol from sugars are principally yeasts capable of withstanding significant osmotic pressures and belonging to the types Moniliella, Aureobasidium, Torulopsis, Candida, Trigonopsis, Trichosporon, and Yallowia . . . without this list being restrictive. These yeasts are preferably chosen from the family of microorganisms called "osmotolerant" and are for example isolated from honey.

In a general manner, the microbiological methods of producing erythritol can implement two different methods of fermentation: the batch method and the continuous method.

In the batch methods, all the substrates necessary for feeding microorganisms are introduced at the start of the fermentation, and the product and the co-products of the fermentation are extracted at the end of fermentation.

Such batch methods of fermentation have been carried out for the production of erythritol, and are described for example in patents EP 136 803 and JP 61-31 091.

However, the drawbacks of the batch methods for the production of erythritol which are found in these two patents are, on the one hand, the long fermentation time, of the order of one to two weeks, and on the other hand, the necessity of managing large volumes of fermentation media, for a productivity which does not exceed 1.5 grams per liter and per hour (g/l/hour) and a yield of the order of 10 to 30%, whence raised production costs.

In the continuous methods, all the fermentation substrates are added in a continuous fashion to the reactor, and fractions of the fermentation medium are extracted at the same rate as the supply of substrates, so as to work at a constant volume.

A continuous method has been used for the production of erythritol and is described in patent U.S. Pat. No. 4,923,812. This method presents the advantage of resolving the majority of the drawbacks of the batch method, and thus permits a gain in productivity and yield which is not inconsiderable.

However, these continuous methods do not make it possible to obtain extremely pure products, since the erythritol extracted is of necessity contaminated by the substrates re-introduced during fermentation.

Thus, for the fermentation of glucose by a colony of Aureobasidium, the values presented in the examples of these two patents illustrate this increase in yield and in productivity since the yields of erythritol are between 45 and 50% and the productivities are of the order of 4 to 4.5 g/l/hour. But with the erythritol produced is also found approximately 10% of non-consumed residual glucose, and, in addition, the high osmotic pressures borne by the microorganism necessarily result in inducing the synthesis of glycerol, ribitol and other polyols with that of the erythritol.

Consequently, the main disadvantage of the continuous methods of fermentation is the necessity of purifying the erythritol. Furthermore, the purification techniques only make it possible to separate with difficulty the erythritol from the co-products of the fermentation, and not any better from the residual sugars not assimilated by the microorganisms.

For this reason, one always finds associated with these methods of continuous fermentation complex, heavy and expensive purification installations.

Moreover, all the specialists agree in recognising that the methods of producing erythritol by fermentation remove certain difficulties which neither the batch method nor the continuous method has totally resolved.

For example, in order to reduce the costs of implementation, all the methods of fermentation are based on the use of fermentation media whose sugar content is maximum.

In fact, the microorganisms producing erythritol can withstand high sugar contents in fermentation substrates. The resultant high osmotic pressures then lead said microorganisms to synthesise polyols including erythritol, but also glycerol, arabitol and/or ribitol.

The problem is that with too high a dose of assimilable sugars, the saturation of the metabolic paths induces the instability of the microbial cultures and a greater mortality of the microorganisms. Furthermore, in these operating conditions, all the microorganisms producing erythritol also produce other polyols in an increased proportion (up to 20% or more ribitol and/or glycerol). In certain cases, when the deviation of the metabolic paths is too significant, the erythritol becomes itself a co-product of the fermentation.

All the efforts of the fermentation experts thus focus on the search for operating conditions which lead to reconciling the best yield and productivity of erythritol of the microorganisms with their level of tolerance to maximum concentrations of sugars.

Besides these standard batch or continuous methods of fermentation, there exists a third method of fermentation called a method of fed-batch fermentation, which is chosen specifically when it is noted that the variation of the concentration in one of the fermentation substrates affects the yield or productivity, which is the case with glucose for the production of erythritol by the fermentation path. This fed-batch system thus makes it possible to resolve the problems linked to inhibition by one of the fermentation substrates.

This method consists in introducing the sugars gradually into the fermentation medium of the microorganisms, not carrying out any decanting, and thus leaving the product in the fermenter, in this case the erythritol, until the end of the fermentation.

Patents EP 136 802 and EP 136 804 describe a method of producing a mixture of polyols (erythritol, glycerol, ribitol), by the fermentation of a sugar, preferably glucose, saccharose, fructose or maltose, by *Moniliella tomentosa* var *pollinis,* using the fed-batch and repeated system. The pre-culture serving to culture the fermenter is possibly removed during a preceding fermentation.

However, patent EP 136 802 gives the fermentation conditions which favour the production of erythritol, glycerol and ribitol from concentrations of sugars, preferably glucose, greater than 30% by weight/volume, and the conditions which favour in particular the production of ribitol by controlling the degree of aeration in the fermentation medium.

Patent EP 136 804 describes, for the production of this same mixture of polyols, the addition of 40 to 80% by weight/volume of sugars to the fermentation medium, the initial concentration of sugars being fixed at between 20 and 35% by weight/volume, with progressive addition such that the total quantity of added sugars is at least 40% by weight/volume.

However, the major problems encountered in the implementation of these methods are the delay in growth of the microorganism, the length of the fermentation which can be as much as twelve days, the time necessary for the total consumption of the substrate, and the presence of co-products which also penalise the yields of erythritol and necessitate carrying out specific purification.

In fact, these methods lead above all to a mixture of erythritol, glycerol and ribitol. Moreover, the use of such high concentrations of sugars (greater than 40% weight/volume) does not make it possible to obtain erythritol easily and principally.

OBJECTS AND SUMMARY OF THE INVENTION

The object of the present invention is therefore to resolve these problems and to supply a method of producing erythritol which responds better than those which exist already to the various constraints of practice.

The method of producing erythritol perfected by the Applicant makes it possible to ensure the almost exclusive production of erythritol, and is based on a succession of fermentations with the intermittent supply of substrates and with recycling of the biomass, keeping a concentration of total sugars at a value lower than 200 g/l.

By concentration of total sugars is meant the sum of the concentrations of residual sugars not consumed by the microorganisms, and the concentrations of sugars introduced by the addition of substrates.

The invention relates more particularly to a method of producing erythritol by fed-batch and repeated fermentation of sugars by microorganisms which produce erythritol, characterised by the fact it comprises the following stages:

a) starting fermentation by introducing said microorganisms into a fermentation medium containing a concentration of sugars lower than 200 g/l, b) continuing the fermentation by carrying out at least one fermentation cycle which comprises:
at least one phase of adding substrates so as to maintain the concentration of total sugars at a value lower than 200 g/l,
at least one phase of separation of the fermentation medium into a concentrated fraction of microorganisms and another fraction enriched with erythritol, after total consumption of the sugars,
at least one phase of recycling recovered and concentrated microorganisms in the fermentation medium, c) collecting all the fractions enriched with erythritol thus obtained.

The first stage a) of the method according to the invention consists in starting the production of erythritol by repeated fed-batch fermentation of sugars by microorganisms producing erythritol, by introducing said microorganisms into a fermentation medium containing a concentration of sugars lower than 200 g/l.

In doing this, the Applicant has overcome a technical prejudice in choosing to use fermentation conditions contrary to those which the specialists recommend using, i.e. with a concentration of sugars clearly lower than the fermentation conditions habitually defined and optimised for the production of erythritol by these osmotolerant microorganisms.

After long research, the Applicant has in fact revealed that for the production of erythritol by the fermentation path, and in order to avoid saturating the metabolic pathways, and producing growth inhibitors, and above all to limit the co-production of other polyols, it was necessary to start the fermentation with concentrations of sugars lower than 200 g/l.

The minimum concentration of sugars necessary for starting the fermentation in acceptable conditions is determined by the chosen microorganism producing erythritol.

For certain microorganisms producing erythritol such as yeasts of the type Moniliella, for example, values of between 100 g/l and 150 g/l will be chosen by preference.

Besides these conditions for starting the fermentation for the production of erythritol, one of the important features of the invention is the control of the additions of substrates to the production media, in order to maintain the concentration of total sugars at a value which does not exceed 200 g/l, and this in order to continue to ensure a preferential production of erythritol.

The second stage b) of the method according to the invention consists then in continuing the fermentation by carrying out at least one fermentation cycle which comprises:

at least one phase of adding substrates so as to maintain the concentration of total sugars at a value lower than 200 g/l,
at least one phase of separation of the fermentation medium into a concentrated fraction of microorganisms and another fraction enriched by erythritol, after total consumption of the sugars,
at least one phase of recycling recovered and concentrated microorganisms in the fermentation medium.

The Applicant has thus had the merit of showing that almost exclusive production of erythritol is maintained by carrying out at least one fermentation cycle in which at least one stage is realised consisting of adding substrates in such a way as to maintain the concentration of total sugars at a value lower than 200 g/l.

This addition of substrates is carried out when the concentration of sugars reaches a minimum value, chosen as a function of the microorganism considered.

The Applicant noticed in fact that the tolerance of the microorganisms to low concentrations of sugars varied from one microorganism to another, for if said microorganisms withstand high concentrations of sugars, their growth is reduced and in certain cases stops when the sugar content of the fermentation medium is low.

Thus the phase of adding sugars is adapted as a function of the fermentative capabilities of the microorganisms considered, and so as to re-introduce substrate when the residual concentration of sugars is sufficiently reduced, even equal to zero, without the growth of the considered microorganisms being retarded or stopped.

For certain microorganisms producing erythritols such as the yeasts of the type Moniliella, for example, preferably the addition of substrates will be carried out when the concentration of total sugars reaches a value of between 0 and 50 g/l.

The addition is carried out at least once, adding each time an additional volume of substrates to the preceding volume of the fermentation.

In accordance with the repeated fed-batch method according to the invention, this additional volume is supplied without decanting the erythritol, which thus continues to accumulate in the fermenter.

One advantage o the method according to the invention is the rapidity of the consumption of the substrate and the high conversion of the sugars, essentially into erythritol, the co-products only being found as traces. In fact, keeping the concentration of sugars to a value which does not exceed 200 g/l leads to its rapid consumption by the microorganisms and thus to increased productivity and richness in erythritol without synthesis of co-products.

The method according to the invention thus makes it possible to reduce considerably the length of each of the stages of fermentation, to ensure an increased richness in erythritol and also to control easily the development of the biomass.

The fermentation cycle of the method according to the invention comprises also at least one phase of separation of the fermentation medium into a concentrated fraction of microorganisms and another fraction enriched with erythritol, after total consumption of the sugars.

This phase makes it possible to provoke above all the total consumption of sugars by the microorganisms producing erythritol, and this stops the fermentation and makes it possible to avoid contaminating the collected erythritol with residual sugars.

The separation between the microorganisms and the fraction enriched with erythritol is carried out by any method known to the person skilled in the art, for example by micro-filtration, using membranes whose pore diameter is adapted to the size of the microorganism considered (at least 1 mm) or by centrifugation in a range from 1000 G to 10000 G.

The clarified solution, enriched with erythritol, obtained at the end of this stage of separation from the microorganisms, constitutes a portion of the erythritol produced.

The fermentation cycle of the method according to the invention comprises finally at least one phase of recycling recovered and concentrated microorganisms in the fermentation medium.

The fermenter is recultured with the biomass thus recovered and concentrated, in order to restart a new fermentation cycle.

The advantage of this stage of recycling the biomass is to reintroduce a biomass, the fermentation capacities of which are intact, and thus to avoid an additional expense, as well as a delay in implementation which would be caused by the preparation of a new culture of microorganisms producing erythritol.

At the end of these sequences of stages, and when the fermentative capabilities of the microorganisms are exhausted, the third stage c) of the method according to the invention consists then in collecting all the fractions enriched with erythritol thus obtained.

The polysaccharides formed in small quantities during the fermentation can be eliminated by classic techniques of ultra- or nano-filtration. As for the low quantities of residual glucose or of fermentation contaminants such as acetoin, they are treated by any known technique, for example by transformation into acids by means of treatment in alkaline conditions at a temperature of between 100° C. and 130° C., for a few minutes to a few hours, depending on the temperature chosen. The acids formed are then easily eliminated during demineralisation.

The recovery of all the erythritol from all the clarified fractions is carried out by any method known per se by the person skilled in the art, for example by concentration at 60% and more, followed by crystallisation of the erythritol, such as described in ROXBURG et al, 1956, Canadian J. Tech., 134, 248–253.

MORE DETAILED DESCRIPTION

Other features and advantages of the invention will appear in reading the non-restrictive example described below.

EXAMPLE

Three 500 ml Erlenmeyer flasks are sown with a culture on a petri dish of microorganisms producing erythritol (in this case a *Monilella tomentosa* colony CBS L61.67 left for 22 hours at 37° C.), the culture medium being composed of 50 g/l glucose, 5 g/l yeast extracts, 5 g/l corn steep liquor, 3 g/l KH2PO4 and 1 g/l MgSO4 and complemented by 10 ml NH4OH at 20%, so as to take the initial pH to a value of 6.

The flasks are placed on an orbital agitator at 150 revolutions per minute (rpm) for twenty hours at 37° C.

The pre-culture thus obtained is introduced into a fermenter of 20 liters kept at 37° C., agitated at 750 rpm and aerated at 15 liters/min, containing 15 l of the culture medium, the composition of which is identical to the medium described above. The length of this sub-culture is 22 hours.

The first fermentation cycle is carried out with constant adjustment of the fermentation in the fermenter of 20 liters to a pH greater than 3.5, with the aid of KOH 5 N and the agitation fixed at 750 rpm and the aeration at 15 liters/min.

Starting said first cycle is carried out in an effective volume of 14.5 liters, containing 1.5 liters inoculum coming from the sub-culture fermenter, 1500 g glucose, to take it to a concentration of 100 g/l in the fermenter, 150 g yeast extracts, 7 g (NH4)2SO4 and 10 ml KOH 5 N making it possible to take the initial pH of this first fermentation cycle to 6.

Two additions of solutions each containing 1500 g glucose are carried out successively after 23 hours (the residual glucose is at a concentration of 50 g/l) and 47 hours (the residual glucose is at a concentration of 27 g/l) of fermentation.

After 75 hours of fermentation, the final volume is 18 liters, and the medium contains 50 g residual glucose and 2000 g erythritol, i.e. a weight yield of 44% and a productivity of 1.5 g/l/h for this first production cycle.
The co-products are:

| TYPE | CONCENTRATION |
| --- | --- |
| Polysaccharides | 0.2% |
| Glycerol | 1% |
| Ribitol | 1% |
| Thehalose | 0.3% |
| Arabitol | — |
| Gluconic acid | — |
| Sorbitol | — |
| Ethanol | — |

The five following hours are used to treat the fermentation must on a module of tangential micro-filtration, functioning with a membrane with a 0.22 mm cutoff threshold. 10 liters of filtrate are recovered and the biomass thus concentrated is recycled in the fermenter.

A new production cycle is then started by a first addition of 8 liters of solution containing 2800 g glucose and 24 g yeast extracts at 80 hours of fermentation (time measured in relation to the hour of starting the fermenting process).

A second addition of 1500 grams of glucose is carried out at 120 hours of fermentation. The level of residual glucose is 50 g/l.

At 150 hours of fermentation, the medium contains 5 g/l residual glucose and 2620 g erythritol, for a volume of 18.6 liters, i.e. for this second cycle, a yield of 42% and a productivity of 1.4 g/l/h.
The co-products are:

| TYPE | CONCENTRATION |
| --- | --- |
| Polysaccharides | 0.3% |
| Glycerol | 2.7% |
| Ribitol | 0.7% |
| Thehalose | 0.3% |
| Arabitol | 0.8% |
| Gluconic acid | — |
| Sorbitol | — |
| Ethanol | — |

The entire must is filtered in the same manner as at the end of the first cycle, and the erythritol obtained is gathered together with the erythritol collected during the first cycle.

What is claimed is:

1. A method of producing erythritol by fed-batch and repeated fermentation of sugars by microorganisms which produce erythritol, comprising the following stages:

a) starting the fermentation by introducing said microorganisms into a fermentation medium containing a concentration of sugars lower than 200 g/l, b) continuing the fermentation after partial or complete assimilation of the sugars by carrying out at least one fermentation cycle which comprises:

at least one phase of adding substrates when the concentration of total sugars reaches a value of between 0 g/l and 50 g/l and still keeping the concentration of total sugars after addition at a value lower than 200 g/l, at least one phase of separating the fermentation medium into a concentrated fraction of microorganisms and another fraction enriched with erythritol, after total consumption of the sugars, at least one phase of recycling recovered and concentrated microorganisms in the fermentation medium, c) collecting all the fractions enriched with erythritol thus obtained.

2. The method according to claim 1, wherein the fermentation is started in stage a) by introducing said microorganisms into a fermentation medium containing a concentration of sugars of between 100 g/l and 150 g/l.

* * * * *